US008029524B1

(12) United States Patent
Mitusina et al.

(10) Patent No.: US 8,029,524 B1
(45) Date of Patent: Oct. 4, 2011

(54) ANGLED ROTARY TISSUE CUTTING INSTRUMENTS AND INNER MEMBERS THEREFOR HAVING FLEXIBLE COUPLINGS

(75) Inventors: Miroslav Mitusina, Ruskin, FL (US); Wilfredo Malave, Lakeland, FL (US); Tihomir Bognar, River View, FL (US); Maria Julie Valles, Ruskin, FL (US)

(73) Assignee: B&M Precision, Inc., Ruskin, FL (US)

( * ) Notice: Subject to any disclaimer, the term of this patent is extended or adjusted under 35 U.S.C. 154(b) by 325 days.

(21) Appl. No.: 11/985,560

(22) Filed: Nov. 15, 2007

(51) Int. Cl.
*A61B 17/32* (2006.01)

(52) U.S. Cl. ........................................ 606/180; 606/167

(58) Field of Classification Search .................. 606/167, 606/169, 170, 171, 180, 59, 159; 464/44, 464/47, 51, 53, 57, 58, 61.1, 62.1; 600/585; 285/222.2, 222.5; 604/22
See application file for complete search history.

(56) References Cited

U.S. PATENT DOCUMENTS

| | | | |
|---|---|---|---|
| 4,646,738 A | 3/1987 | Trott | |
| 6,053,922 A | 4/2000 | Krause et al. | |
| 6,312,438 B1 | 11/2001 | Adams | |
| 6,344,037 B1 | 2/2002 | Suorsa et al. | |
| 6,526,645 B2 * | 3/2003 | Romano | 29/435 |
| 6,533,749 B1 | 3/2003 | Mitusina et al. | |
| 6,656,195 B2 | 12/2003 | Peters et al. | |
| 6,860,849 B2 * | 3/2005 | Matsushita et al. | 600/140 |

* cited by examiner

*Primary Examiner* — Anhtuan Nguyen
*Assistant Examiner* — Katherine M Shi

(57) ABSTRACT

A flexible inner tubular member for rotation within an angled outer tubular member of a rotary tissue cutting instrument includes a distal end having a cutting element, a proximal end connectible with a powered surgical handpiece, and a flexible coupling between the distal end and the proximal end for transmitting torque to rotate the cutting element while conforming to the angled configuration of the outer member. The flexible coupling comprises inner, middle and outer spiral members, each formed of a flat strip of material, alternately wound in opposite rotational directions. The strips of material that form the inner and outer spiral members have a width intentionally and measurably different from the width of the strip of material that forms the middle spiral member.

17 Claims, 3 Drawing Sheets

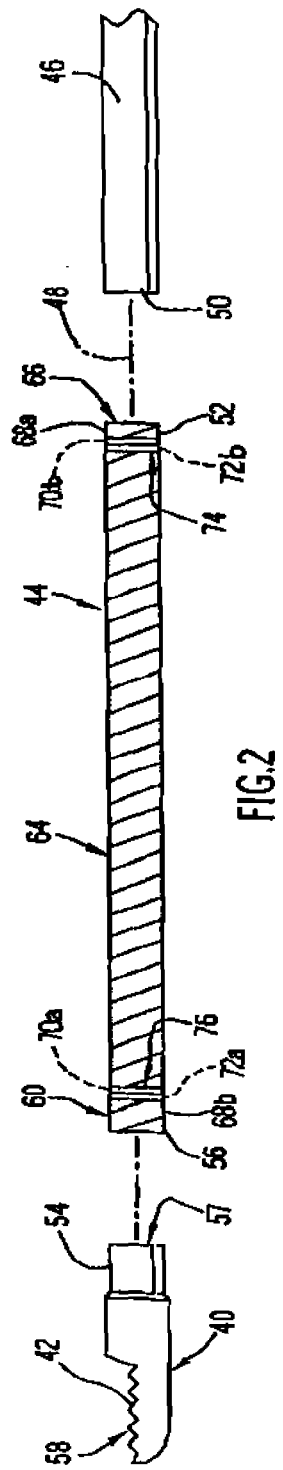
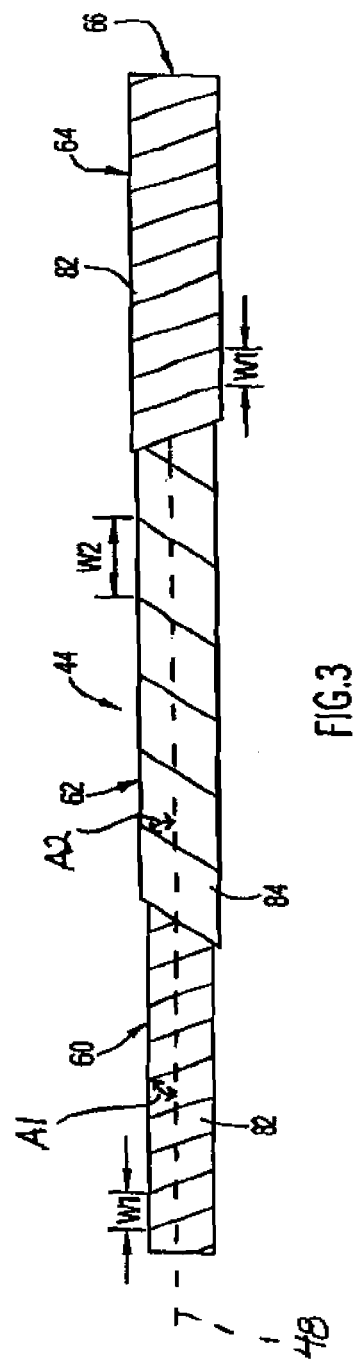

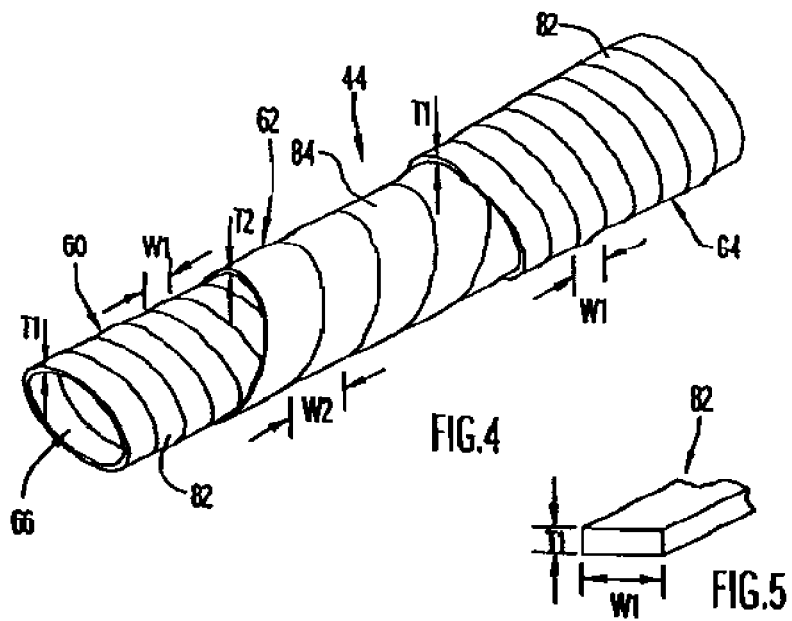
FIG.4
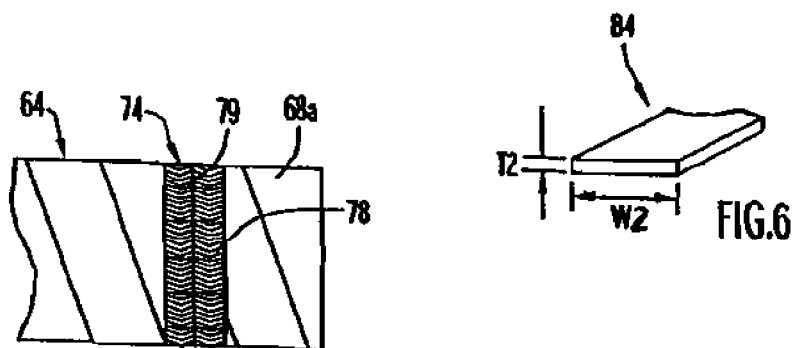
FIG.5
FIG.7
FIG.6
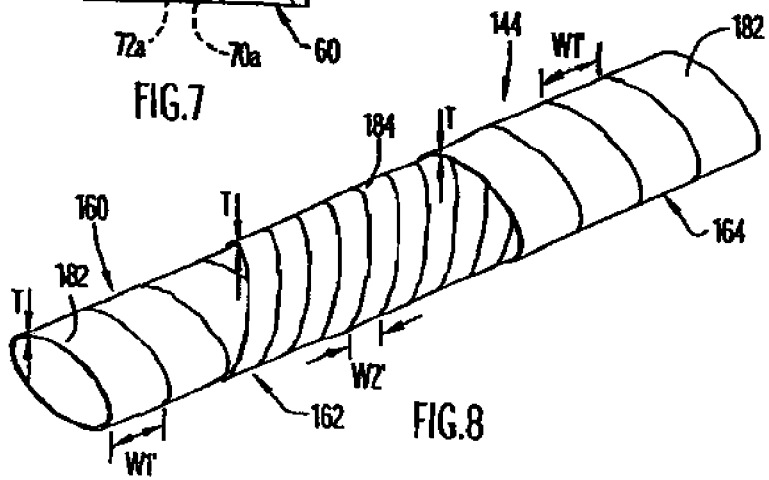
FIG.8

ANGLED ROTARY TISSUE CUTTING INSTRUMENTS AND INNER MEMBERS THEREFOR HAVING FLEXIBLE COUPLINGS

BACKGROUND OF THE INVENTION

1. Field of the Invention

The present invention pertains generally to flexible tubular inner members of angled rotary tissue cutting instruments and, more particularly, to flexible tubular inner members having flexible couplings for transmitting torque to rotate a cutting element at the distal end of the inner member in an angled rotary tissue cutting instrument.

2. Brief Discussion of the Related Art

Rotary tissue cutting instruments have become well accepted for use in cutting anatomical tissue at surgical sites in many various surgical procedures, especially those in which access to the surgical site is gained through a relatively narrow or small size natural or artificially created passage. Rotary tissue cutting instruments are typically characterized by an elongate tubular outer member having a distal end with an opening therein defining a cutting port or window for receiving anatomical tissue, and by an elongate tubular inner member that has a distal cutting element positioned for rotation past the cutting window. The tubular inner member is rotatably disposed within the tubular outer member to rotate the cutting element to cut the anatomical tissue received in the cutting window. Proximal ends of the outer and inner members are normally attached to hubs that are engageable with a powered surgical handpiece having a motor that rotates the inner member relative to and within the outer member. The cutting window of the outer member and the cutting element of the inner member can each have various configurations. The outer member cutting window can be provided with a cutting edge or formation that cooperates with a cutting edge or formation of the inner member cutting element to cut the anatomical tissue.

Rotary tissue cutting instruments in which the outer member is longitudinally or axially straight are unsuitable for accessing some surgical sites. It has therefore been recognized to provide angled rotary tissue cutting instruments in which the tubular outer member is longitudinally bent, angled or curved in order to facilitate positioning of the distal end of the instrument at the surgical site as represented by U.S. Pat. No. 4,646,738 to Trott, U.S. Pat. No. 6,312,438 B1 to Adams, U.S. Pat. No. 6,533,749 B1 to Mitusina et al and U.S. Pat. No. 6,656,195 B2 to Peters et al. In angled rotary tissue cutting instruments, the inner member normally has a flexible region disposed within the bend, angle or curve of the outer member that transmits torque to rotate the cutting element while conforming to the bent, angled or curved configuration of the outer member.

Various designs have been proposed for the flexible regions used in the inner members of angled rotary tissue cutting instruments, including designs involving multiple spirals. The aforementioned Trott patent describes a flexible transmission interconnecting a distal end portion and a proximal end portion of the tubular inner member of a rotary surgical tool, where the flexible transmission is composed of three spirals, i.e. an inner spiral, a middle spiral and an outer spiral, alternately wound in opposite directions and spot-welded together at opposite ends. The spirals are made from flat stainless steel ribbons which are apparently the same width for each spiral as well as being the same thickness for each spiral. The rotary surgical tool disclosed in the Trott patent was marketed under the name of "Merlin" and was limited to operation with the outer member bent to a maximum of only about a 15 degree angle. Furthermore, it was found that the spirals of the flexible transmission could undesirably stretch prior to assembly of the inner member with the outer member. In practice, an inner member in which the flexible transmission had undesirably stretched would be discarded and not used, thereby necessitating a replacement inner member and resulting in increased cost.

The aforementioned Adams, Mitusina et al and Peters et al patents disclose tubular inner members of angled rotary tissue cutting instruments that have flexible regions composed of a helical or spiral cut formed in the body of an inner tube, and inner and outer spiral wraps disposed over the helically cut region of the inner tube. Flat strips of material are used to form the inner and outer spiral wraps, the strips apparently being the same width for both the inner and outer spiral wraps and apparently being the same thickness for both the inner and outer spiral wraps.

U.S. Pat. No. 6,053,922 to Krause et al discloses a flexible shaft for transmitting rotary power from a driven end to a driven part along a non-straight path, particularly the medullary canal of the femur. The flexible shaft is characterized by a helical or spiral slot cut in a tube in a pattern defining interlocked adjacent tube segments, without any spiral wrap being disposed over the slotted region of the tube.

U.S. Pat. No. 6,344,037 B1 to Suorsa et al pertains to an integrated coaxial transmission line and flexible drive cable for use in catheter systems and including inner wound and outer wound wires disposed over a core. The inner and outer wound wires have a round cross-section as opposed to a rectangular cross-section as found in a flat strip of material.

SUMMARY OF THE INVENTION

The present invention is generally characterized in an angled rotary tissue cutting instrument and a flexible inner tubular member for rotation within an angled outer tubular member of a rotary tissue cutting instrument. The angled rotary tissue cutting instrument comprises an elongate tubular outer member including an elongate tubular outer body having a distal end with an opening therein, a proximal end attached to an outer member hub, and an angled, curved or bent length portion between the distal end and the proximal end. The flexible inner tubular member includes an elongate tubular inner body having a distal end with a cutting element, a proximal end attached to an inner member hub, and a flexible coupling between the distal end and the proximal end of the inner body. The inner member is rotatably receivable within the outer member with the flexible coupling disposed within the angled length portion and the cutting element exposed from the opening to cut anatomical tissue when the inner member is rotated within and relative to the outer member. The flexible coupling disposed within the angled length portion transmits torque to rotate the cutting element while conforming to the angled, curved or bent configuration of the outer body. The flexible coupling comprises inner, middle and outer spiral members, each formed of a flat strip of material, alternately wound in opposite rotational directions. The strips of material that form the inner and outer spiral members have a width intentionally and measurably different from the width of the strip of material that forms the middle spiral member. In one embodiment of the flexible coupling, the width of the strips of material that form the inner and outer spiral members is less than the width of the strip of material that forms the middle spiral member. In another embodiment of the flexible coupling, the width of the strips of material that form the inner and outer spiral members is greater than the width of the strip of material that forms the middle spiral member. The strips of material that form the inner, middle and outer spiral members can all be of the same thickness. Alternatively, the strips of material that form the inner and outer spiral members can have a thickness intentionally and measurably different than the thickness of the strip of material that forms the middle spiral member. In one embodiment of the flexible coupling, the strips of material that form the inner and outer spiral members are of the same thickness, and the thickness of the strip of material that forms the middle spiral member is greater than the thickness of the strips of material that form the inner and outer spiral members. In another embodiment, the strips of material that form the inner and outer spiral members are of the same thickness, but the strip of material that forms the middle spiral member has a thickness less than the thickness of the strips of material that form the inner and outer spiral members. The width of the strips of material that form the inner and outer spiral members is preferably in the range of 0.050 inch-0.090 inch and the width of the strip of material that forms the middle spiral member is preferably in the range of 0.050 inch-0.090 inch but intentionally and measurably different from the width of the strips of material that form the inner and outer spiral members. The thickness of the strips of material that form the inner, middle and outer spiral members is preferably in the range of 0.003 inch-0.006 inch. The strips of material that form the inner and outer spiral members can be of the same thickness within the range of 0.003 inch-0.006 inch, and the thickness of the strip of material that forms the middle spiral member can be in the range of 0.003 inch-0.006 inch but intentionally and measurably different from the thickness of the strips of material that form the inner and outer spiral members.

Various objects, advantages and benefits of the present invention will become apparent from the following description of preferred embodiments taken in conjunction with the drawings.

BRIEF DESCRIPTION OF THE DRAWINGS

FIG. 2 is an exploded side view of the tubular inner member of FIG. 1.

FIG. 3 is a broken cut-away side view of the flexible coupling of the tubular inner member.

FIG. 4. is a broken cut-away perspective view of the flexible coupling.

FIG. 5 is a broken perspective view of a flat strip of material used to form an inner spiral member and an outer spiral member of the flexible coupling shown in FIG. 4, or alternatively used to form a middle spiral member of an alternative flexible coupling.

FIG. 6 is a broken perspective view of a flat strip of material used to form a middle spiral member of the flexible coupling of FIG. 4, or alternatively used to form the inner spiral member and the outer spiral member of the alternative flexible coupling.

FIG. 7 is an enlarged, broken side view in detail of an end weld of the flexible coupling.

FIG. 8 is a broken cut-away perspective view of another alternative flexible coupling according to the present invention.

DESCRIPTION OF THE PREFERRED EMBODIMENTS

Figure 1:
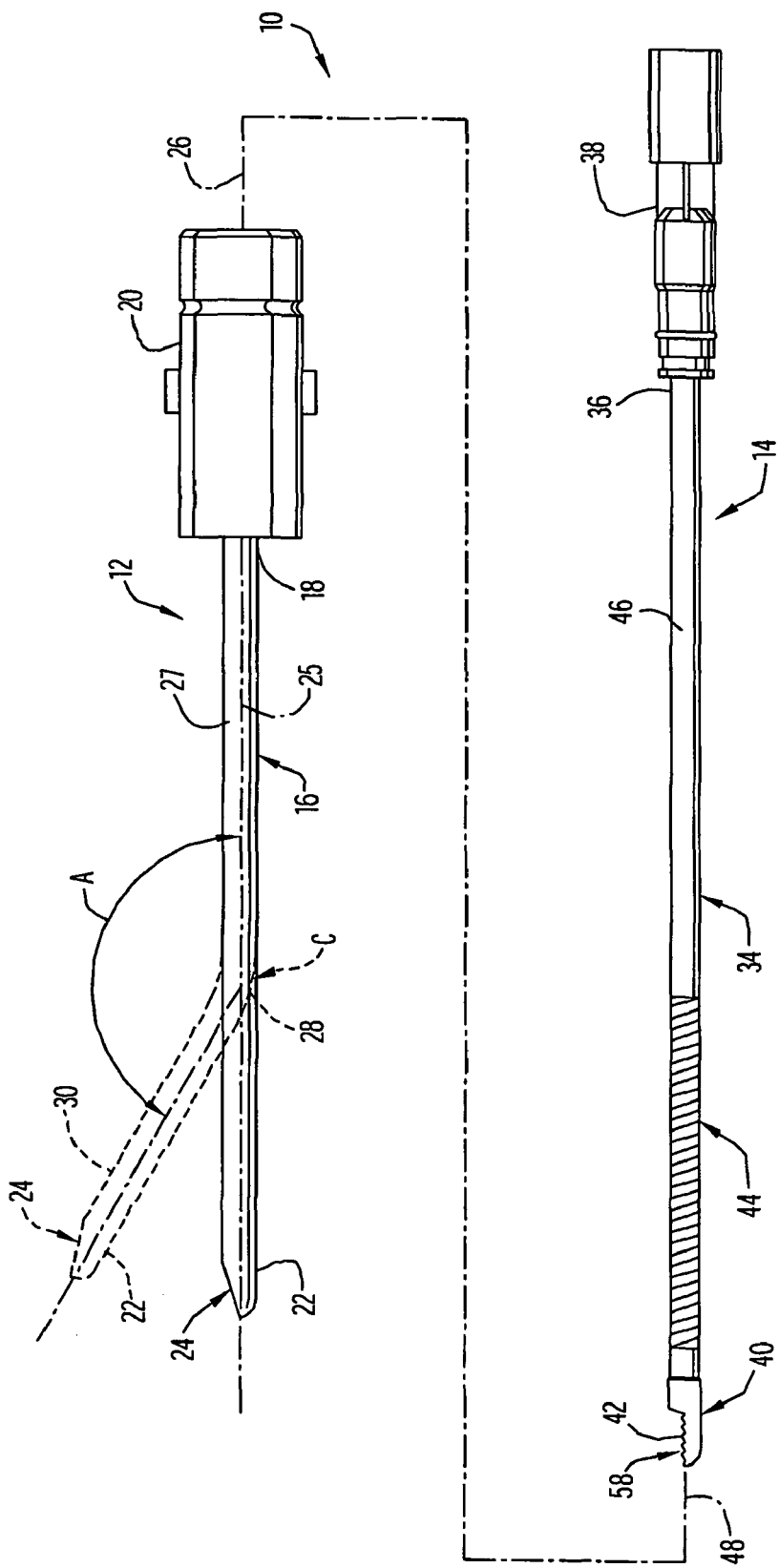
FIG. 1 is an exploded side view of an angled rotary tissue cutting instrument in which the tubular inner member thereof includes a flexible coupling in accordance with the present invention.

A rotary tissue cutting instrument 10 is depicted in FIG. 1 and comprises a flexible elongate tubular inner member according to the present invention. The rotary tissue cutting instrument 10 includes an elongate tubular outer member 12 and the flexible elongate tubular inner member 14 for being rotatably disposed or received within the outer member. The outer member 12 comprises an elongate tubular outer body 16 having a proximal end 18 attached to an outer member hub 20 and having a distal end 22 with an opening 24 therein. The opening 24 communicates with an internal passage 25 that extends longitudinally through the outer member 12. In the case of outer member 12, the opening 24 defines a cutting port or window for receiving anatomical tissue, and the opening 24 faces laterally at an acute angle with a central longitudinal axis 26 of the outer member. The outer body 16 is preferably made of stainless steel acceptable for medical use. The opening 24 in the distal end 22 that defines the cutting window can have various peripheral configurations and can face in various directions. As described further below, a cutting element of the inner member 14 is rotatable past the cutting window defined by opening 24 to cut anatomical tissue received in the cutting window. The opening 24 can be formed as a cutting element having one or more cutting edges, cutting surfaces or cutting formations to cooperate with the cutting element of the inner member to cut anatomical tissue.

The outer body 16 may initially be in a longitudinally or axially straight configuration and may be bent, angled or curved from the longitudinally straight configuration as shown in dotted lines in FIG. 1 so that the rotary tissue cutting instrument 10 is an angled rotary tissue cutting instrument. As explained further below, the outer body 16 can be bent, angled or curved from the longitudinally straight configuration while the inner member 14 is already disposed within the outer member 12. Subsequent to being bent, angled or curved, the outer body 16 will be in a longitudinally or axially non-straight configuration or, in other words, will have a bent, angled or curved configuration. In the longitudinally non-straight configuration shown in FIG. 1, the outer body 16 defines a proximal length portion 27 of longitudinally or axially straight configuration extending distally from the hub 20 to a bent, angled or curved length portion 28, and a distal length portion 30 of longitudinally or axially straight configuration extending from the angled length portion 28 to the distal end 22. The angled length portion 28 connects the proximal length portion 27 to the distal length portion 30 so that the distal length portion 30 is oriented at a bend angle A relative to the central longitudinal axis of the proximal length portion 27. In FIG. 1, the distal length portion 30 is depicted as being angled upwardly from the proximal length portion 27, which is coaxial with the axis 26, but it should be appreciated that the distal length portion can be angled from the proximal length portion in any desired direction including upward, downward and lateral directions. In addition, it should be appreciated that the radius of curvature C for the angled length portion 28, the size of the bend angle A, the location of the bend, angle or curve relative to the distal end 22 of the outer member, and the direction of the bend angle A may vary depending on the procedure to be performed and the location of the surgical site to be accessed with the distal end of the instrument.

The tubular inner member 14 comprises an elongate tubular inner body 34 having a proximal end 36 attached to an inner member hub 38 and having a distal end 40 including a cutting element 42. The inner member 14 is insertable in the internal passage 25 of the outer member 12 to position the cutting element 42 for exposure from the opening 24 to contact and cut anatomical tissue. In the case of instrument 10, the cutting element 42 is positioned for rotation past the cutting window defined by opening 24 to cut anatomical tissue received in the cutting window. The cutting element 42 can have various configurations and can include one or more cutting edges, cutting surfaces or cutting formations for cutting anatomical tissue contacted with the cutting element as it rotates. The cutting edges, cutting surfaces or cutting formations of the cutting element 42 can cooperate with one or more cutting edges, cutting surfaces or cutting formations on the distal end 22 of the outer member 12 to cut the anatomical tissue. The cutting element 42 for inner member 14 is illustrated as comprising a plurality of cutting teeth. When the inner member 14 is disposed or received within the outer member 12 with the cutting element 42 positioned to cut anatomical tissue, the inner member hub 38 will be disposed proximally of the outer member hub 20, and the hubs 20 and 38 are engageable with a powered surgical handpiece (not shown) used to rotate the inner member 14 relative to and within the outer member 12. Powered surgical handpieces as conventionally used in rotary tissue cutting instruments typically include a motor having a rotatable drive shaft engageable with the inner member hub to effect rotation of the inner member relative to and within the outer member.

The elongate tubular inner body 34 of the inner member 14 includes a flexible coupling 44 for being disposed within the angled length portion 28 of the outer member 12 to transmit torque from the proximal end 36 to the distal end 40 to rotate the cutting element 42 while conforming to the bent, angled or curved configuration of the outer member 12. The flexible coupling 44 extends longitudinally between the distal end 40 and the proximal end 36. As depicted in FIGS. 1 and 2, the flexible coupling 44 for inner member 14 is disposed between and extends longitudinally between the distal end 40 and a proximal length portion 46 of the inner body 34. The proximal length portion 46 defines the proximal end 36 of the inner body 34 which is attached to the inner member hub 38 and is of longitudinally or axially straight configuration coaxial with a central longitudinal axis 48 for being disposed within the proximal length portion 27 of the outer body 16. The proximal length portion 46 extends distally from the hub 38 to a terminal attachment end 50 of the proximal length portion 46 that is joined or attached to a terminal proximal end 52 of the flexible coupling 44. The proximal length portion 46 comprises a tube and is preferably made of stainless steel acceptable for medical use. The distal end 40 comprises the cutting element 42 and a terminal attachment end 54 that is joined or attached to a terminal distal end 56 of the flexible coupling 44. The distal end 40 can be hollow or formed with an internal passage or cavity 57, and can be provided with an opening 58 in communication with the internal passage or cavity 57. The distal end 40 is preferably made of stainless steel acceptable for medical use.

As best seen in FIGS. 3 and 4, the flexible coupling 44 comprises a plurality of spiral or helical members, the plurality of spiral or helical members consisting of an inner spiral or helical member 60, a middle spiral or helical member 62 concentrically and closely disposed over the inner spiral member 60, and an outer spiral or helical member 64 concentrically and closely disposed over the middle spiral member 62. An internal longitudinal passage 66 extends longitudinally through the flexible coupling 44 and is defined by the interior of the inner spiral member 60. The inner spiral member 60 has a rearward end 68a and a forward end 68b opposite its rearward end. The middle spiral member 62 has a rearward end 70a and a forward end 70b opposite its rearward end. The outer spiral member 64 has a rearward end 72a and a forward end 72b opposite its rearward end. All three spiral members 60, 62 and 64 are united or joined at, adjacent or near their rearward ends 68a, 70a and 72a by a proximal union or joint 74. All three spiral members 60, 62 and 64 are united or joined at, adjacent or near their forward ends 68b, 70b and 72b by a distal union or joint 76 as depicted in FIG. 2. The rearward ends 70a and 72a of the middle and outer spiral members 62 and 64 may terminate at or within the proximal joint 74, and the rearward end 68a of the inner spiral member 60 may extend rearwardly or proximally beyond the proximal joint 74 as seen in FIGS. 2 and 7. Similarly, the forward ends 70b and 72b of the middle and outer spiral members 62 and 64 may terminate at or within the distal joint 76, and the forward end 68b of the inner spiral member 60 may extend distally or forwardly beyond the distal joint 76 as depicted in FIG. 2. The proximal joint 74 preferably comprises a circumferential weld 78 extending 360 degrees about the central longitudinal axis 48 of the flexible coupling 44 as best depicted in FIGS. 2 and 7. The weld 78 can be formed to define a circumferential junction 79 located at or about the mid-point of the width of the weld. The circumferential junction 79 may be spaced a predetermined distance distally from the terminal edge of the rearward end 68a of the inner spiral member 60. The distal joint 76 preferably comprises a circumferential weld 78 extending 360 degrees about the central longitudinal axis 48 of the flexible coupling 44. In the case of flexible coupling 44, the distal joint weld is the same or essentially the same as the proximal joint weld except that the circumferential junction 79 of the distal joint weld is spaced a predetermined distance proximally from the terminal edge of the forward end 68b of the inner spiral member 60 that is greater than the distance that the circumferential junction of the proximal joint weld is spaced distally from the terminal edge of the rearward end 68a of the inner spiral member 60. It should be appreciated, however, that the location of the joints 74 and 76 and the amount of extension of the ends 68a and 68b of the inner spiral member 60 beyond the joints can vary. The rearward and forward ends 68a and 68b of the inner spiral member 60 that extend beyond the proximal and distal joints 74 and 76, respectively, are engageable with the attachment ends 50 and 54, respectively, of the proximal length portion 46 and the distal end 40 to join attach or assemble the flexible coupling 44 to the proximal length portion 46 and to the distal end 40 in order to form the tubular inner body 34. Preferably, the proximal end 52 and the distal end 56 of the flexible coupling 44 are joined, attached or assembled to the attachment ends 50 and 54 of the proximal length portion 46 and the distal end 40, respectively, by laser welding. It should be appreciated that the length of the flexible coupling 44 and/or the distance between the joints 74 and 76 can vary depending on the length of the angled length portion 28 of the outer member 12 and the length needed for the flexible coupling to conformably reside within the angled length portion 28.

When the terminal proximal end 52 and the terminal distal end 56 of the flexible coupling 44 are attached or joined to the terminal attachment ends of the proximal length portion 46 and the distal end 40, respectively, to form the tubular inner body 34 of the inner member 14 as seen in FIG. 1, the longitudinal passage 66 through the flexible coupling 44 is in communication with the lumen of the tube of the proximal length portion 46 and with the internal cavity or passage 57 of the distal end 40, which is in communication with the opening 58, to form an interior longitudinal passage within the inner body 34. The interior longitudinal passage of the inner body 34 has a diameter along the flexible coupling 44 corresponding to the diameter of the interior of the inner spiral member 60. Hence, the inner diameter of the inner body 34 along the flexible coupling 44 corresponds to the diameter of the interior of inner spiral member 60, and the outer diameter of the inner body 34 along the flexible coupling 44 corresponds to the diameter of the exterior of the outer spiral member 64. The inner member hub 38 may be provided with an interior passage in communication with the lumen of the tube of the proximal length portion 46 such that a suction or aspiration channel formed of the interior passages of the inner body 34 and inner member hub 38 is defined within and/or through the inner member 14 for communication with a surgical site via the opening 58. The suction or aspiration channel enables fluid and anatomical tissue to be aspirated from the surgical site in a manner conventional to rotary tissue cutting instruments.

Each spiral member 60, 62 and 64 is made from a flat strip of material, preferably a flat strip of stainless steel acceptable for medical use including 302 stainless steel, full hard. Flat strips of material 82 are used to form the inner spiral member 60 and the outer spiral member 64. As seen in FIGS. 4 and 5, the strips of material 82 used to form the inner and outer spiral members 60 and 64 have a width W1 and a thickness T1. The strips of material 82 have a rectangular cross-section with the width W1 defined between planar sides of the strips and the thickness T1 defined between planar top and bottom surfaces of the strips. A flat strip of material 84 is used to form the middle spiral member 62. The strip of material 84 has a width W2 and a thickness T2 as best seen in FIGS. 4 and 6. The strip of material 84 has a rectangular cross-section with the width W2 defined between planar sides of the strip and the thickness T2 defined between planar top and bottom surfaces of the strip. The width W1 of the strips of material 82 used for the inner spiral member 60 and for the outer spiral member 64 is intentionally and measurably different from the width W2 of the strip of material 84 used for the middle spiral member 62. In the case of flexible coupling 44, the strips of material 82 used to form the inner and outer spiral members 60 and 64 have a width W1 that is less than the width W2 of the strip of material 84 used to form the middle spiral member 62. Furthermore, in the case of flexible coupling 44, the thickness T1 of the strips of material 82 used for the inner spiral member 60 and for the outer spiral member 64 is intentionally and measurably different from the thickness T2 of the strip of material 84 used for the middle spiral member 62. In particular, the thickness T1 of the strips of material 82 that form the inner and outer spiral members 60 and 64 is greater than the thickness T2 of the strip of material 84 that forms the middle spiral member 62.

The inner spiral member 60 may be formed by winding a strip of material 82 in a spiral or helical path upon a cylindrical mandrel that is coaxial with the axis 48. The inner spiral member 60 winds or turns in a first rotational direction about the central longitudinal axis 48, with the sides of the strip of material 82 at a pitch or angle with the axis 48 and the width W1 of the strip of material 82 oriented parallel to the axis 48. In the case of flexible coupling 44, the inner spiral member 60 winds about the central longitudinal axis 48 in a clockwise direction, i.e. with a right hand turn, looking distally, from the rearward end 68a to the forward end 68b. Opposite ends of the strip of material 82 form the rearward and forward ends 68a and 68b of the inner spiral member 60. The angle or pitch for the inner spiral member 60 may vary. In the case of flexible coupling 44, the inner spiral member 60 defines a pitch or angle A1 of about 80 degrees with the central longitudinal axis 48.

The middle spiral member 62 may be formed by winding the strip of material 84 over or on top of the inner spiral member 60 while the inner spiral member 60 remains disposed upon the cylindrical mandrel. The strip of material 84 is wound directly over or on top of the inner spiral member 60 in a spiral or helical path but winds or turns in a second rotational direction, opposite the rotational direction of the inner spiral member 60, with the sides of the strip of material 84 at a pitch or angle with the axis 48 and the width W2 of the strip of material 84 oriented parallel to the axis 48. In the case of flexible coupling 44, the middle spiral member 62 winds about the central longitudinal axis 48 in a counterclockwise direction, i.e. with a left hand turn, looking distally, from the rearward end 70a to the forward end 70b. Opposite ends of the strip of material 84 form the rearward and forward ends 70a and 70b of the middle spiral member 62. The pitch or angle for the middle spiral member 62 may vary. In the case of flexible coupling 44, the middle spiral member 62 defines a pitch or angle A2 of about 60° with the central longitudinal axis 48.

The outer spiral member 64 may be formed by winding a strip of material 82 directly over or on top of the middle spiral member 62 while the middle spiral member 62 and the inner spiral member 60 remain disposed upon the cylindrical mandrel. The outer spiral member 64 winds or turns in a spiral or helical path about the central longitudinal axis 48 in the same rotational direction as the inner spiral member 60, with the sides of the strip of material 82 at the same pitch or angle A1 as the inner spiral member 60 and the width W1 of the strip of material 82 oriented parallel to the axis 48. Accordingly, in the case of flexible region 44, the outer spiral member 64 winds about the central longitudinal axis 48 in a clockwise direction, i.e. with a right hand turn, looking distally, from the rearward end 72a to the forward end 72b. Opposite ends of the strip of material 82 form the rearward and forward ends 72a and 72b of the outer spiral member 64. The flexible coupling 44 composed of the three layers of concentrically overlapping spiral members has an outer diameter that fits closely within the outer body 16 and is concurrent with the outer diameter of the distal end 40.

In one preferred embodiment for flexible coupling 44, the width W1 of the strips of material 82 that form the inner spiral member 60 and the outer spiral member 64 is 0.050 inch; the width W2 of the strip of material 84 that forms the middle spiral member 62 is 0.090 inch; the thickness T1 of the strips of material 82 used to form the inner spiral member 60 and the outer spiral member 64 is 0.006 inch; and the thickness T2 of the strip of material 84 used to form the middle spiral member 62 is 0.003 inch. However, the width W1 of the strips of material used to form the inner and outer spiral members 60 and 64 can be within the range of 0.050 inch-0.090 inch, and the width W2 of the strip of material used to form the middle spiral member 64 can be in the range of 0.050 inch-0.090 inch but is measurably and intentionally different from the width W1. The thickness of the strips of material 82 used to form the inner and outer spiral members 60 and 64 can be in the range of 0.003 inch-0.006 inch and the thickness of the strip of material 84 used to form the middle spiral member 64 can be in the range of 0.003 inch-0.006 inch. The thickness T1 can be measurably and intentionally different from the thickness T2 or, as described further below, the thickness T1 of the strips of material that form the inner and outer spiral members 60 and 64 can be the same as the thickness T2 of the strip of material that forms the middle spiral member 62.

An alternative flexible coupling for the inner member 14 can be obtained using strips of material 84, in place of the strips of material 82, to form the inner spiral member 60 and the outer spiral member 64, respectively, and using a strip of material 82, in place of the strip of material 84, to form the middle spiral member 62. In this case, the width of the strips of material that form the inner and outer spiral members is greater than the width of the strip of material that forms the middle spiral member. Also, the thickness of the strips of material that form the inner and outer spiral members is less than the thickness of the strip of material that forms the middle spiral member.

Another alternative flexible coupling 144 for use in the inner member 14 is depicted in FIG. 8 but without the proximal and distal ends of the flexible coupling being shown. The flexible coupling 144 is similar to the flexible coupling 44 except that the strips of material 182 used to form the inner spiral member 160 and the outer spiral member 164 have a width W1' that is greater than the width W2' of the strip of material 184 used to form the middle spiral member 162, and the strips of material 182 that form the inner and outer spiral members 162 and 164 have a thickness T that is the same as the thickness T of the strip of material 184 that forms the middle spiral member 162. In a preferred embodiment for the flexible coupling 144, the width W1' of the strips of material 182 is 0.090 inch; the width W2' of the strip of material 184 is 0.050 inch; and the thickness T is 0.003 inch. However, the width W1' of the strips of material that form the inner and outer spiral members 160 and 164 can be in the range of 0.050 inch-0.090 inch; the width W2' of the strip of material that forms the middle spiral member 162 can be in the range of 0.050 inch-0.090 inch but smaller than the width W1'; and the thickness T that is the same for all three spiral members 160, 162 and 164 can be in the range of 0.003 inch-0.006 inch.

An additional alternative flexible coupling for the inner member 14 can be obtained using strips of material 184, in place of the strips of material 182, to form the inner spiral member 160 and the outer spiral member 164, respectively, and using a strip of material 182, in place of the strip of material 184, to form the middle spiral member 162. In this case, the width of the strips of material that form the inner and outer spiral members is greater than the width of the strip of material that forms the middle spiral member while the strips of material that form the inner, middle and outer spiral members are all the same thickness.

The inner member 14 can be inserted in the outer member 12 with the outer body 16 in the longitudinally straight configuration shown in solid lines in FIG. 1, and the outer body 16 can be bent, angled or curved from the longitudinally straight configuration to assume the longitudinally non-straight configuration while the inner body 34 is disposed within the outer body 16. The outer body 16 can be bent at a location coincident with the flexible coupling 44 so that the flexible coupling 44 resides within the angled length portion 28 obtained by bending the outer body 16 and conforms to the bend, angle or curve of the angled length portion 28. Of course, it should be appreciated that the inner member 14 could be slidably inserted in the outer member 12 after the outer body 16 has been bent to assume the bent, angled or curved configuration. The outer and inner member hubs 20 and 38 are engageable with a powered surgical handpiece used to rotate the inner member 14, typically at high rotational speeds, relative to and within the outer member 12. The flexible coupling 44 disposed within the angled length portion 28 of the outer body 16 transmits torque from the handpiece to the distal end 40 to rotate the cutting element 42 to cut anatomical tissue. The flexible coupling 44 conforms to the angled, bent or curved configuration of the outer body 16 as the inner member 14 rotates within the outer member 12. The flexible coupling 44 is capable of transmitting torque to the cutting element 42 when the inner member 14 is rotated in either the clockwise or counterclockwise direction. It should be appreciated that the inner member 14 can be used with the longitudinally straight outer body 16 as a straight rotary tissue cutting instrument.

An inner member having the flexible coupling comprised of three spiral members alternately wound in opposite rotational directions with the middle spiral member formed of a strip of material having a width intentionally and measurably different from the width of the strips of material that form the inner and outer spiral members meets the torque and speed requirements required for tissue cutting in various surgical procedures while allowing its use in outer members bent at an increased range of bend angles. In particular, an inner member having the flexible coupling of the present invention is especially advantageous for use in angled tissue cutting instruments having outer members bent at bend angles A greater than 30°, but its advantages extend to use in angled tissue cutting instruments having outer members bent at bend angles A in the range of or about 14° to 47°, and bend angles A up to about 60° are possible. Moreover, the flexible coupling resists stretching and the loss of integrity that results from stretching. Where the middle spiral member is formed of a wider strip of material and the inner and outer spiral members are formed of the narrower strips of material, an inner member of increased flexibility is obtained for outer member bend angles in the range of or about 25° to 47°. Where the middle spiral member is formed of a narrower strip of material and the inner and outer spiral members are formed of the wider strips of material, a more sturdy and rugged inner member is obtained for outer member bend angles in the range of or about 14° to 33°. Depending on the surgical application, various characteristics including torque transmission, operational speed, flexibility and/or robustness can be enhanced by using strips of material of the same thickness for all three spiral members, or by forming the middle spiral member from a strip of material having a thickness that is intentionally and measurably different from the thickness of the strips of material that form the inner and outer spiral members.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An angled rotary tissue cutting instrument comprising
an elongate tubular outer member including an outer member hub and an elongate tubular outer body having a distal end with an opening therein, a proximal end attached to said outer member hub, and an angled length portion between said distal end and said proximal end; and
an elongate tubular inner member including an inner member hub and an elongate tubular inner body having a distal end with a cutting element, a proximal end attached to said inner member hub, a flexible coupling extending longitudinally between said distal end and said proximal end of said inner body and coupling said distal end of said inner body to said proximal end of said inner body, and an interior passage extending longitudinally within said inner body, said inner member being rotatably receivable within said outer member with said flexible coupling disposed within said angled length portion and said cutting element exposed from said opening to cut anatomical tissue when said inner member is rotated within said outer member, said flexible coupling comprising a plurality of spiral members, said plurality of spiral members consisting of an inner spiral member formed of a single flat strip of material wound in a first rotational direction, a middle spiral member disposed directly over said inner spiral member and formed of a single flat strip of material wound in a second rotational direction, opposite said first rotational direction, and an outer spiral member disposed directly over said middle spiral member and formed of a single flat strip of material wound in said first rotational direction, said flexible coupling having a terminal forward end attached to a terminal attachment end of said distal end of said inner body and having a terminal rearward end attached to a terminal attachment end of said proximal end of said inner body whereby said flexible coupling couples said distal end to said proximal end to form said inner body, said interior passage having a diameter along said flexible coupling defined by the interior of said inner spiral member, said strips of material of said inner spiral member and said outer spiral member each having a width equal to a first width and a thickness equal to a first thickness, and said strip of material of said middle spiral member having a width equal to a second width and a thickness equal to a second thickness, said first width being less than said second width and said first thickness being greater than or equal to said second thickness, said flexible coupling transmitting torque to rotate said cutting element to cut anatomical tissue while conforming to said angled length portion of said outer body.

2. An angled rotary tissue cutting instrument comprising an elongate tubular outer member including an outer member hub and an elongate tubular outer body having a distal end with an opening therein, a proximal end attached to said outer member hub, and an angled length portion between said distal end and said proximal end; and an elongate tubular inner member including an inner member hub and an elongate tubular inner body having a distal end with a cutting element, a proximal end attached to said inner member hub, a flexible coupling extending longitudinally between said distal end and said proximal end of said inner body and coupling said distal end of said inner body to said proximal end of said inner body, and an interior passage extending longitudinally within said inner body, said inner member being rotatably receivable within said outer member with said flexible coupling disposed within said angled length portion and said cutting element exposed from said opening to cut anatomical tissue when said inner member is rotated within said outer member, said flexible coupling comprising a plurality of spiral members, said plurality of spiral members consisting of an inner spiral member formed of a single flat strip of material wound in a first rotational direction, a middle spiral member disposed directly over said inner spiral member and formed of a single flat strip of material wound in a second rotational direction, opposite said first rotational direction, and an outer spiral member disposed directly over said middle spiral member and formed of a single flat strip of material wound in said first rotational direction, said flexible coupling having a terminal forward end attached to a terminal attachment end of said distal end of said inner body and having a terminal rearward end attached to a terminal attachment end of said proximal end of said inner body whereby said flexible coupling couples said distal end to said proximal end to form said inner body, said interior passage having a diameter along said flexible coupling defined by said inner spiral member, said strips of material of said inner spiral member and said outer spiral member each having a width equal to a first width and a thickness equal to a first thickness, and said strip of material of said middle spiral member having a width equal to a second width and a thickness equal to a second thickness, said first width being greater than said second width and said first thickness being less than or equal to said second thickness, said flexible coupling transmitting torque to rotate said cutting element to cut anatomical tissue while conforming to said angled length portion of said outer body.

3. The angled rotary tissue cutting instrument recited in claim 1 wherein said outer body comprises a longitudinally straight proximal length portion extending distally from said outer member hub to said angled length portion, and a longitudinally straight distal length portion extending distally from said angled length portion to said distal end of said outer body, said angled length portion defining an angle with said proximal length portion in the range of about 14° to about 60°.

4. The angled rotary tissue cutting instrument recited in claim 3 wherein said proximal end of said inner body comprises a longitudinally straight proximal length portion extending distally from said inner member hub to said attachment end of said proximal end of said inner body that is attached to said rearward end of said flexible coupling, said proximal length portion of said inner body being disposed within said proximal length portion of said outer member when said inner body is rotatably received in said outer member.

5. The angled rotary tissue cutting instrument recited in claim 4 wherein said flexible coupling further includes a proximal joint adjacent said rearward end of said flexible coupling joining rearward ends of said strips of material of said inner spiral member, said middle spiral member and said outer spiral member, and a distal joint adjacent said forward end of said flexible coupling joining forward ends of said strips of material of said inner spiral member, said middle spiral member and said outer spiral member.

6. The angled rotary tissue cutting instrument recited in claim 5 wherein said proximal joint and said distal joint are circumferential welds.

7. The angled rotary tissue cutting instrument recited in claim 6 wherein said rearward end of said strip of material of said inner spiral member extends proximally beyond said proximal joint and said forward end of said strip of material of said inner spiral member extends distally beyond said distal joint.

8. The angled rotary tissue cutting instrument recited in claim 1 wherein said first width is within the range of 0.050 inch to 0.090 inch, and said second width is within the range of 0.050 inch to 0.090 inch but is greater than said first width, and said first thickness and said second thickness are in the range of 0.003 inch to 0.006 inch.

9. The angled rotary tissue cutting instrument recited in claim 2 wherein a said first width within the range of 0.050 inch to 0.090 inch, and said second width is within the range of 0.050 inch to 0.090 inch but is less than said first width, and said first thickness and said second thickness are in the range of 0.003 inch to 0.006 inch.

10. The angled rotary tissue cutting instrument recited in claim 8 wherein said second width is 0.090 inch and said first width is 0.050 inch.

11. The angled rotary tissue cutting instrument recited in claim 10 wherein said first thickness is equal to said second thickness.

12. The angled rotary tissue cutting instrument recited in claim 10 wherein said second thickness is less than said first thickness.

13. The angled rotary tissue cutting instrument recited in claim 12 wherein said second thickness is 0.003 inch and said first thickness is 0.006 inch.

14. The angled rotary tissue cutting instrument recited in claim 9 wherein said second width is 0.050 inch and said first width is 0.090 inch.

15. The angled rotary tissue cutting instrument recited in claim 14 wherein said first thickness is equal to said second thickness.

16. The angled rotary tissue cutting instrument recited in claim 14 wherein said second thickness is greater than said first thickness.

17. The angled rotary tissue cutting instrument recited in claim 16 wherein said second thickness is 0.006 inch and said first thickness is 0.003 inch

\* \* \* \* \*